US00PP11851P2

(12) United States Plant Patent
Cosner

(10) Patent No.: US PP11,851 P2
(45) Date of Patent: May 1, 2001

(54) IMPATIENS PLANT NAMED 'ELRED'

(75) Inventor: Harlan B. Cosner, Broadbent, OR (US)

(73) Assignees: Harlan Cosner; Sue Cosner, both of Broadbent, OR (US); husband and wife, as joint tenants with right of survivorship ( * ) Notice: Subject to any disclaimer, the term of this patent is extended or adjusted under 35 U.S.C. 154(b) by 0 days.

(21) Appl. No.: 09/169,592

(22) Filed: Oct. 9, 1998

(51) Int. Cl.[7] ..... A01H 5/00

(52) U.S. Cl. ..... Plt./318

(58) Field of Search ..... Plt./318; 800/323

(56) References Cited

PUBLICATIONS

Hartmann et al. Plant Propagation: Principles and Practices, 6th Edition. Simon and Schuster, New Jersey. pp. 244–249, 1997.*

* cited by examiner

*Primary Examiner*—Bruce R. Campell
*Assistant Examiner*—Melissa L. Kimball
(74) *Attorney, Agent, or Firm*—Bradley M. Ganz, Esq.

(57) ABSTRACT

A new and distinctive New Guinea Impatiens plant characterized by flowers with two or more colors distributed in distinct irregular randomly distributed patterns on some or all petals and flowers. The patterns are defined by multiple irregularly shaped regions of color. Generally, each region consists of an elongate streak or patch of color typically radiating in a direction from the base of a petal to the edge of the petal. The irregularly shaped regions, while not necessarily exclusive of other colors, generally are dominated by a single color. The streaks or patches forming regions may vary in color intensity, shape, length, and width. They also vary in terms of their position relative to the base and edge of a petal.

2 Drawing Sheets

The present invention relates to a new and distinct cultivar botanically known as *Impatiens hawkeri*, commercially as New Guinea Impatiens, and by the cultivar name ElRed.

Figure 1:
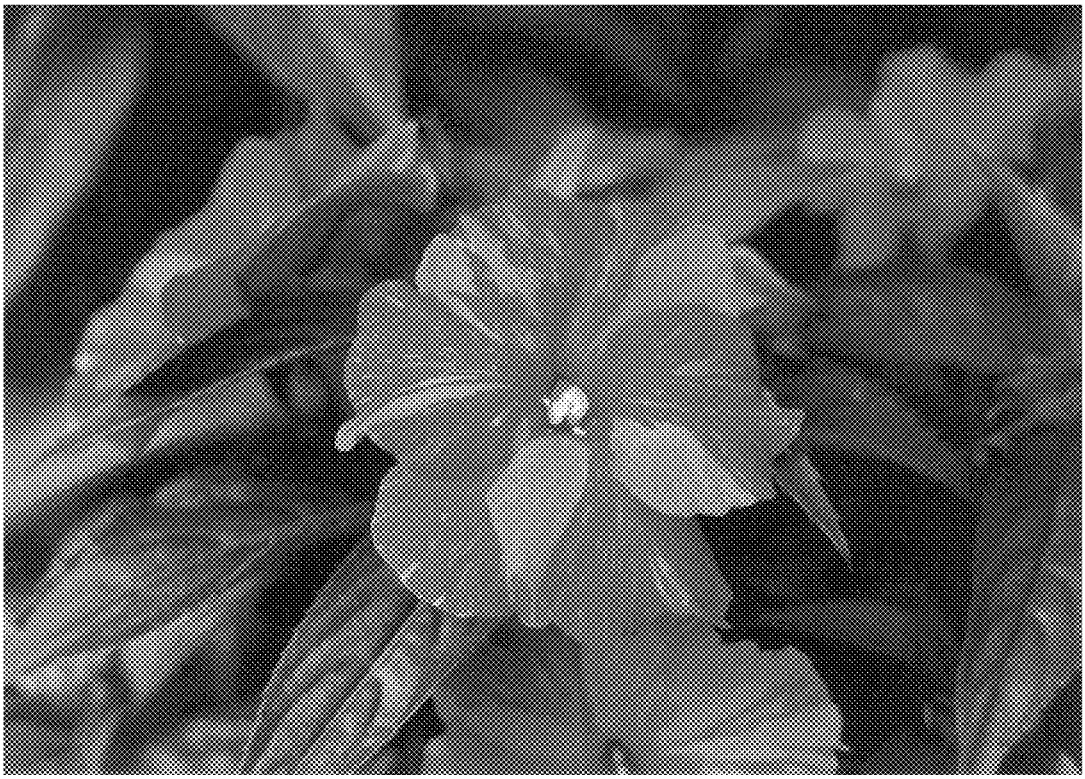
Figure 2:
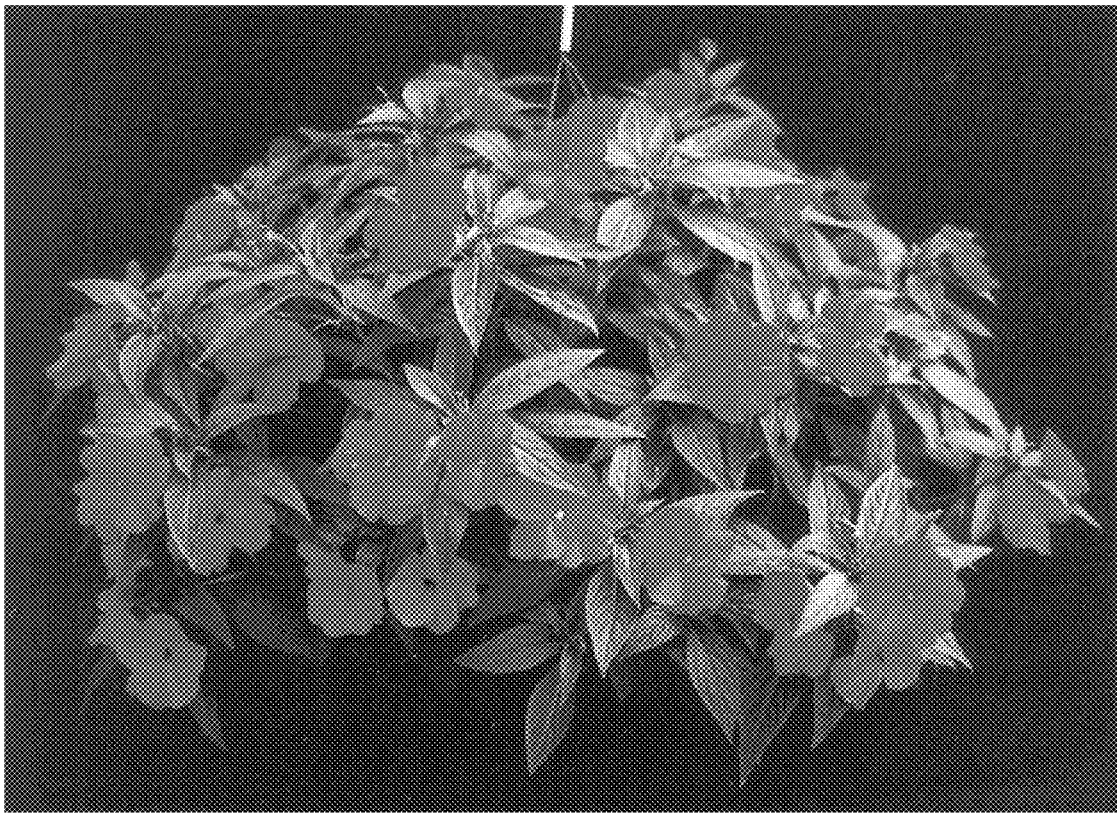

The cultivar of FIGS. 1–2 was developed and selected in a controlled breeding program in a controlled environment in Coquille, Ore. by the inventor, Harlan Cosner. 'ElRed' was selected as a single lateral branch of an unnamed parent, coded L-146. Further details of a method of breeding flowers with the new and distinct characteristics of 'ElRed' are disclosed in a co-pending utility patent application, filed concurrently on the same date as this application, naming Harland Cosner as the inventor, entitled Novel Impatiens Plants And Methods Of Reproduction, Ser. No. 09/169,593 (hereinafter the "Cosner Utility Application"). The disclosure of that application is hereby incorporated by reference for the plants and flowers disclosed and the methods of producing the same.

Asexual reproduction of the new cultivar, based on terminal cuttings taken at Coquille, Ore. and grown out in a controlled environment there, shows that the unique features of 'ElRed' are stable and reproduced true to type in successive generations of asexual reproduction.

FIGS. 1–2 show New Guinea Impatiens plants according to the present invention. Relative to single or multi-color flowers of conventional New Guinea impatiens plants, such as the Star or Bright Eye varieties, which have distinct non-random patterns, the colors on flowers of the present invention are distributed in distinct irregular, randomly distributed patterns on some or all petals of some or all flowers. The patterns are defined by multiple, irregularly-shaped regions of color. Generally, each region consists of an elongate streak or patch of color typically radiating in a direction from the base of a petal to the edge of the petal. The irregularly shaped regions, while not necessarily exclusive of other colors, generally are dominated by a single color. The streaks or patches forming regions may vary in shape, length, width, and color intensity. They also may vary in terms of their position relative to the base and edge of a petal. As used herein, the term "marbled" and variations of this word shall refer to a petal or flower having patterns as described in this paragraph.

The present cultivar differs from its parent in that predominantly every flower displays a random multi-colored pattern on nearly every petal of nearly every flower. The parent plant produced flowers with petals that were extremely variable from solid different colors to the current random multi-colored patterns of the present invention.

Color references are according to The Royal Horticultural Society Colour Chart, except where general terms of ordinary dictionary significance are used.

The photographs of the plant and flowers in FIGS. 1–2, which correspond to FIGS. 2–3 in the Cosner Utility Application, were taken at Coquille, Ore. in late summer/early fall. They illustrate the new and distinctive marbled effect in the flowers of 'ElRed'. The photographs show the marbled effect in the flowers, colors in the flowers, foliage of the plant, and habit of the plant as true as reasonably possible. Flower and foliage colors in the photographs may appear different from the actual colors due to variables such as light reflectance and photo-processing conditions. To the extent there may be differences between the photographs and the Colour Chart descriptions in the text, the textual descriptions control.

FIG. 1 is a photograph of a flower according to the present invention.

FIG. 2 is a photograph of three plants each of which is a clone having the same identification code, L-146-3. The plants are third generation clones from the plant coded L-146. The three plants shown in FIG. 2 are in a 10" container. (Code numbers used herein correspond to the ones given in the Cosner Utility Application, and identify the same plants when the same.)

The following description of the plant and flowers in the photographs is based on the environmental and cultural practices at Coquille Ore. The photographs were taken during late summer/early fall. The following measurements, values, and comparisons describe plants grown under a double layer of polyethylene with controlled temperatures typically ranging from about 58° F. to about 85° F. Light levels ranged from about 3500 to 7000 ft. candles. The individual plants were grown in six (6") Azalea containers in a soiless medium of the Peatlite type. Fertility of the medium was 20-10-20 western special plus, minor trace elements applied at 175 PPM of Nitrogen constant feed, no leach.

The plants of the present invention have not been grown under all conditions. If the plants of the present invention are grown under other conditions, some phenotypical variations may result, as may occur with any plant.

Parentage

The parent of the plant of the present invention was a sport from a controlled cross between female parent coded S-108 and male parent coded S-486A, both of which are proprietary seedlings of the inventor produced in a controlled breeding program. The coded plants are shown in the lineages described in FIGS. 11–13 of the Cosner Utility Application, and described in the text accompanying those figures.

Propagation:

*Type cutting.*—Lateral tips of plants were the cuttings used for asexual reproduction.

*Time to initiate roots.*—Approximately 14 to 21 days with shorter time in summer and longer time in winter.

*Rooting habit.*—The rooting habit is characterized by numerous, fibrous, and well-branched roots.

Plant description: FIG. 2 illustrates the overall plant characteristics, which are described in more detail below:

*Plant form and habit.*—Medium vigorous, mounded to wide, upright vase shaped; a free branching habit with numerous large flowers per plant; shiny, dark green foliage: flowers held above or beyond the foliage; a compact to medium-compact growth habit. Mature plants are about 22 to 28 cm. in height, and about 28 to 35 cm. in width. Both of these measurements are a function of age, the above environmental and cultural practices, and can vary accordingly.

*Branches.*—The habit is free branching. Branches are about 0.5 cm diameter in the internodes and about 1.0 cm at the nodes. The branch lengths and internode lengths vary with plant age, environment, and cultural practices. Color is translucent in type measuring 146B–C in the internodes, with a reddish appearance at nodes measuring close to 178A.

*Foliage shape.*—Shape is oblong lanceolate; cuneate to attenuate base; accuminate apex; serrate margin. Size of largest is about 12 cm long; 4 cm wide.

*Foliage color.*—Shiny adaxial surface 147A; abaxial surface of 147B; abaxial surface venation, main vein 152A at base and 146A toward apex, lateral veins are barely distinguishable; abaxial surface venation main vein 148B at base, darkening to 148A toward apex, with laterals close to 146A on the mature foliage. Juvenile foliage adaxial surface is 147A; abaxial surface is 147B; adaxial surface venation in main vein is 146C at base becoming indistinguishable at apex, lateral veins are indistinguishable; abaxial surface main vein is 146B at base, darkening to 146A toward apex, lateral veins are closest to 146A.

*Petioles.*—About 1.5 cm. long on largest leaves, half round, about 3 mm wide on top, depth of about 2 mm. Color on top is close to 152A to B with occasional reddish markings close to 178A; bottom color is 146B.

Flower description:

The following flower traits have been repeatedly observed and are determined to be the unique characteristics of 'ElRed'.

*Flowering type and habit.*—Flowers in which predominantly every petal has a marbling effect as defined in the text above, illustrations of which are shown in the photographs. The photographs show flowers with multicolor marbling where the random multi-colored patterns are primarily comprised of shades of a reddish purple and salmony pink to salmony orange with none being either dominant or in a fixed position. Free flowering and continuous.

*Natural flowering season.*—Year round in greenhouse.

*Flowers borne.*—Beyond foliage, arising from leaf axils.

*Flower and bud colors.*—Adaxial surface has random markings of 51A, 50A, 61B and 71B, with a darker mark at base of 60A. Abaxial surface of the top petal has the typical center ridge which is close to 187B. The remainder of this petal and the other 4 petals have random markings close to 61C, 63A, and 43C. Buds prior to opening are top 187B, sepals are as described. Solid color petals or flowers may occur that match one of the above colors. In commercial production it is expected that generally about 15% or less of the flowers may have one or more petals of a substantially solid color matching one of the above colors. Less than about 10% of the branches may produce flowers that are not marbled as described, but may be substantially solid colors matching one of the above colors.

*Quantity of flowers.*—Usually 4 to 8 per whorl, with normally 17 to 25 open per plant at a time.

*Typical flower and bud sizes.*—Flowers are about 7 cm. wide; 7 cm. high; 1.25 cm. deep. The top center petal is about 5 cm wide and 3 cm deep; reniform in shape with rounded to retuse apex and entire margin. Each side petal is about 3.5 cm. wide and 3.5 cm. long; shape is reverse cordate with a cuneate base, a retuse apex, and entire margin. Each lower petal is about 4 cm. wide and 3.5 cm. long; deltoid in shape with a cuneate base, retuse apex, and entire margin. The side and lower petals are fused at the base. The above measurements refer to the larger flowers. The buds prior to opening are about 2.25 cm in length; about 1.5 cm in diameter; shape is ovoid.

*Peduncles.*—About 5 cm. long; 2 mm. in diameter; colored on top close to 166B, bottom close to 145B, close to 141C where attached at axil.

*Spur.*—About 7 cm. long, and 3 mm. in diameter at sepal end; shape is acicular, curved tube wider at sepal end. Color is 187C at sepal end with a greenish tip close to 145B.

*Sepals.*—3; one attached to the spur measuring about 1.7 cm. wide, and 2 cm long; rounded oval in shape with a pointed apex; adaxial surface is marked randomly with 63B and a lighter whitish-pink color with 63A toward apex end; the abaxial surface is randomly marked close to 63B and 62B with a greenish tip close to 144B. Each other sepal is about 7 mm. wide and 1.8 cm. in length; both surfaces appear close in coloration, with the adaxial surface being more translucent; markings are of 185B and 142C with an elongated tip of 143A to B.

*Reproductive organs.*—Ovary is colored 143A; about 6 mm. in length; 2 mm. in diameter; stigma is whitish green translucent; about 2 mm wide. The anther is a single fused organ wrapped around the ovary with 5 spur-like attachments at the base; colored 185A at the base, and 161D at the top. The pollen color is closest to 4D. The pollen and anther are both shed prior to the stigma being receptive to the sperm nucleus of the pollen; natural seed production seldom occurs as a result.

Disease resistance: Problems from fungal, bacterial, or viral pathogens have not been observed.

Seed production: Plants are self-sterile.

The above description of the prior art should be referred to. Due to the uniqueness of the coloration of 'ElRed', no other New Guinea impatiens are believed to exist with which the cultivar can be reasonably compared. This uniqueness is best shown in the figures.

What is claimed:

1. A new and distinct New Guinea impatiens plant called ElRed, characterized by its exhibition of marbled flowers, substantially as shown and described herein.

* * * * *